(12) United States Patent
Muller et al.

(10) Patent No.: US 12,106,470 B2
(45) Date of Patent: Oct. 1, 2024

(54) LESION DETECTION AND LOCALIZATION IN HETEROGENEOUS MEDIA

(71) Applicant: North Carolina State University, Raleigh, NC (US)

(72) Inventors: Marie Muller, Raleigh, NC (US); Thomas Egan, Raleigh, NC (US); Kaustav Mohanty, Raleigh, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 427 days.

(21) Appl. No.: 17/299,676

(22) PCT Filed: Dec. 3, 2019

(86) PCT No.: PCT/US2019/064217
§ 371 (c)(1),
(2) Date: Jun. 3, 2021

(87) PCT Pub. No.: WO2020/117789
PCT Pub. Date: Jun. 11, 2020

(65) Prior Publication Data
US 2022/0036546 A1    Feb. 3, 2022

Related U.S. Application Data

(60) Provisional application No. 62/774,463, filed on Dec. 3, 2018.

(51) Int. Cl.
*G06T 7/00* (2017.01)
*A61B 8/00* (2006.01)
(Continued)

(52) U.S. Cl.
CPC .............. *G06T 7/0012* (2013.01); *A61B 8/08* (2013.01); *A61B 8/4488* (2013.01); *G06T 7/136* (2017.01);
(Continued)

(58) Field of Classification Search
CPC ................... G06T 7/0012; G06T 7/136; G06T 2207/10132; G06T 2207/20024;
(Continued)

(56) References Cited

U.S. PATENT DOCUMENTS 4,817,015 A    3/1989  Insana et al.
8,814,795 B2   8/2014  Derode et al.
(Continued)

FOREIGN PATENT DOCUMENTS

WO    2019104340 A1    5/2019

OTHER PUBLICATIONS

International Search Report dated Feb. 21, 2020 in co-pending PCT Application No. PCT/US2019/064217 filed Dec. 3, 2019.
(Continued)

*Primary Examiner* — Dhaval V Patel
(74) *Attorney, Agent, or Firm* — Thomas | Horstemeyer, LLP

(57) ABSTRACT

An ultrasound system and method are provided for detecting lesions and/or abnormalities in a heterogeneous medium. An array of ultrasound transducer elements configured to emit ultrasound signals and to receive backscattered ultrasound signals. A processor performs a lesion detection algorithm that processes the backscattered ultrasound signals to obtain an Inter-element Response Matrix (IRM), splits the IRM into a plurality of sub-IRMs corresponding to subsets of the ultrasound transducer elements, and then performs additional processing that includes performing a depression detection algorithm to identify one or more lesions and/or abnormalities.

20 Claims, 11 Drawing Sheets

(51) Int. Cl.
*A61B 8/08* (2006.01)
*G06T 7/136* (2017.01)

(52) U.S. Cl.
CPC ............ *G06T 2207/10132* (2013.01); *G06T 2207/20024* (2013.01); *G06T 2207/30096* (2013.01)

(58) Field of Classification Search
CPC ............ G06T 2207/30096; A61B 8/08; A61B 8/4488; A61B 8/085; A61B 8/4483; G01S 15/8977; G01S 15/8915
See application file for complete search history.

(56) References Cited

U.S. PATENT DOCUMENTS

| | | | |
|---|---|---|---|
| 9,888,879 B1* | 2/2018 | Cho | A61B 5/0095 |
| 10,267,914 B2 | 4/2019 | Trottier | |
| 2011/0125014 A1* | 5/2011 | Derode | G01S 15/8977 |
| | | | 600/437 |
| 2011/0125023 A1 | 5/2011 | Palti | |
| 2013/0109971 A1 | 5/2013 | Dahl et al. | |
| 2014/0364733 A1 | 12/2014 | Huang et al. | |
| 2014/0364738 A1* | 12/2014 | Huang | A61B 8/5207 |
| | | | 600/447 |
| 2016/0078614 A1* | 3/2016 | Ryu | G06T 7/12 |
| | | | 382/128 |

OTHER PUBLICATIONS

Anand et al., "Monitoring Formation of High Intensity Focused Ultrasound (HIFU) Induced Lesions using Backscattered Ultrasound", Mar. 16, 2004, pp. 88-94, https://asa.scitation.org.doi/pdf/10.1121/1.1652131.

Kawasaki et al., "Noninvasive Quantitative Tissue Characterization and Two-Dimensional Color-Coded Map of Human Atherosclerotic Lesions Using Ultrasound Integrated Backscatter," Aug. 31, 2001, pp. 486-492, http://www.onlinejacc.org/content/accj/38/2/486.full,pdf.

* cited by examiner

VASELINE NODULE IN SPONGE

LESION DETECTION AND LOCALIZATION IN HETEROGENEOUS MEDIA

CROSS-REFERENCE TO RELATED APPLICATIONS

The present application is a U.S. National Phase filing under 35 U.S.C. 371 of PCT international application No. PCT/US2019/064217 filed on Dec. 3, 2019, which claims the benefit of, and priority to, the filing date of U.S. provisional application Ser. No. 62/774,463, filed on Dec. 3, 2018 and entitled "LESION IMAGING AND DETECTION IN MULTIPLE SCATTERING MEDIA," both of which are incorporated by reference herein in their entireties.

GOVERNMENT SUPPORT

This invention was made with support from the National Institutes of Health under Grant No. R21 CA231503. The Government has certain rights in this invention.

TECHNICAL FIELD

The invention relates to an ultrasound system and method for detecting lesions and/or abnormalities.

BACKGROUND

Ultrasound imaging using linear array transducers works on echolocation. For non-destructive evaluation of any medium, a plane wave is emitted and the received signal is used to map the medium. The physics behind the formation of the image are based on the linear relationship of the arrival time t of the wave and the distance d between the transducer element and the scatterer, $t=2d/c$. When a wave is sent into a porous, heterogeneous and a strongly scattering medium, the received echoes have two major contributions: Single scattering and multiple scattering. The linearity between distance and time is maintained when single scattering is a dominant feature. However, in complex, highly heterogeneous media, due to the presence of a high scatterer density, multiple scattering plays a major role in the propagation of the wave, thereby destroying the linearity between d and t. Also, when the size of the scatterer is comparable to the wavelength, the wave is scattered at every encounter with a scatterer. This further enhances multiple scattering as well as attenuation. In that context, classical imaging methods fail. Imaging porous heterogeneous media has remained a challenge due to the failure of traditional imaging modalities, higher attenuation, domination of multiple scattering over single scattering and loss in distance-time linearity. These challenges have posed a substantial restriction on the application of ultrasound in non-destructive evaluation (NDE) of heterogeneous materials, crack size imaging and prediction in polycrystalline materials, lung nodule imaging, etc.

Some methods have been developed to image strongly scattering, complex media. A full matrix capture (FMC) approach was developed and tested on aluminum blocks with notches placed at different depths. The FMC approach combined with total focusing method (TFM) improved the signal-to-noise ratio and has shown promise in imaging complex media. Since it has been established that it is the multiple scattering contribution which leads to the failing of traditional imaging modalities, work has been performed on separating the single and multiple scattering contributions in backscattered waves, which played a major role in the further development of imaging techniques for random media. Once the separation of single and multiple scattering is performed, a DORT (French acronym for decomposition of the time-reversal operator) method was applied that was combined with a single scattering filter in order to devoid it of any multiple scattering contribution. This algorithm was tested in a medium containing randomly distributed steel rods (diameter of 0.8 mm). A target (diameter of 15 mm) to be imaged was placed behind the medium, whose thickness was more than three times the transport mean free path (l*).

Another known approach combined DORT and TFM approaches with a multiple scattering filter to image polycrystalline media and detect the presence of a flaw/crack or notch. A nickel-based alloy with notches of radius 1 mm placed at different depths was inspected using a 64 element linear array operating at a central frequency of 5 MHz. The results showed that the TFM approach alone had a low flaw detection rate. However applying DORT along with a multiple scattering filter exhibited high detection fidelity with an acceptable signal-to-noise ratio.

It is interesting to note that all of the methods described above are completely different from traditional ultrasound B-Scan imaging techniques. In all of the methods, an ultrasound linear array, composed of independent programmable emitters and receivers, is used. The data acquisition takes place by firing individual elements one by one and receiving from all elements to obtain an Inter-element Response Matrix. To image a heterogeneous medium, reducing the multiple scattering contribution is very important. Multiple element arrays provide a great improvement and flexibility. In medical applications, beamforming and TFM improve the single to multiple scattering contribution. However in media where the scattering is purely dominated by multiple scattering, coherent beamforming fails. As waves progress in random media with very strong scatterers, they diffuse slowly rather than they propagate, which can be characterized by the diffusion constant (D). Previous work showcased the applicability of extracting the incoherent intensity of the backscattered wave and calculating D to be a highly accurate method to characterize heterogeneous media such as the lung parenchyma and melamine sponge foams. Although this previous work allows the assessment of the diffusion constant in a heterogeneous medium, it does not provide imaging capabilities, because of the non-local feature of the diffusion constant.

A need exists for an ultrasound solution capable of detecting weakly scattering regions in highly scattering media.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
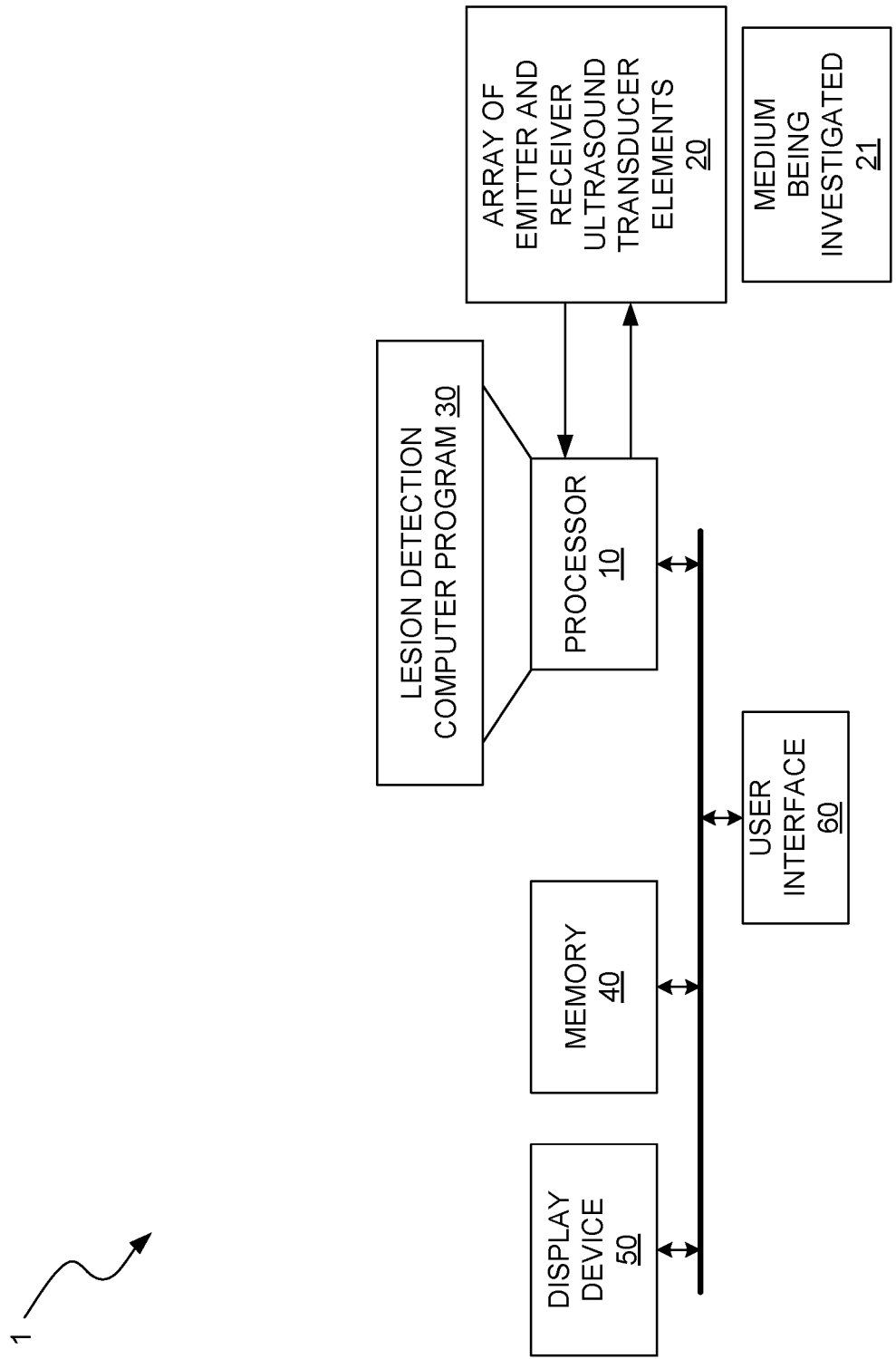
FIG. 1 is a block diagram of the ultrasound system for detecting and localizing lesions in accordance with a representative embodiment.

The present disclosure is directed to an ultrasound system and method for detecting and localizing lesions and abnormalities in a heterogeneous medium. An array of ultrasound transducer elements emits ultrasound signals and receives backscattered ultrasound signals. A processor performs a detection algorithm that processes the backscattered ultrasound signals to obtain an Inter-element Response Matrix (IRM), splits the IRM into a plurality of sub-IRMs corresponding to subsets of the ultrasound transducer elements, and then performs additional processing that includes performing a depression detection algorithm to identify and localize one or more lesions.

Aspects in Accordance with Inventive Principles and Concepts

In accordance with one aspect, the ultrasound system comprises an array of ultrasound transducer elements configured to emit ultrasound signals and to receive backscattered ultrasound signals and a processor configured to perform a lesion detection algorithm. The processor comprises first processing logic configured to process the received backscattered ultrasound signals to obtain an Inter-element Response Matrix (IRM), second processing logic configured to split the IRM into a plurality of sub-IRMs corresponding to subsets of the ultrasound transducer elements, third processing logic configured to process the sub-IRMs to separate a coherent intensity contribution from an incoherent intensity contribution, fourth processing logic configured to process the coherent intensity contribution to obtain a diffusion constant, and fifth processing logic configured to perform a depression detection algorithm that processes the diffusion constant to identify one or more lesions.

In accordance with another aspect, the array is a one-dimensional (1-D) array.

In accordance with another aspect, the array is a two-dimensional (2-D) array.

In accordance with another aspect, the array is a linear array.

In accordance with another aspect, the array is a curved array.

In accordance with another aspect, the depression detection algorithm performed by the fifth processing logic identifies a plurality of potential lesions and detects a depression depth of each identified lesion. In this case, the processor further comprises sixth processing logic configured to perform a thresholding operation that only treats the detected lesion having the greatest depression depth as a real lesion. In accordance with another aspect, the processor further comprises seventh processing logic configured to perform a Gaussian filter operation on the lesion that has the greatest depth to approximate a location and a size of the lesion that has the greatest depth.

In accordance with another aspect, the processor comprises first processing logic configured to process the received backscattered ultrasound signals to obtain an IRM, second processing logic configured to split the IRM into a plurality of sub-IRMs corresponding to subsets of the ultrasound transducer elements, third processing logic configured to process the sub-IRMs to separate single scattering contributions from multiple scattering contributions, and fourth processing logic configured to process information obtained from at least one of the single scattering contribution and the multiple scattering contribution to identify one or more lesions.

In accordance with another aspect, the information obtained from at least one of the single scattering contribution and the multiple scattering contribution consists of a ratio of the single scattering contribution to the multiple scattering contribution, and the fourth processing logic performs a depression detection algorithm that processes the ratio to identify one or more lesions.

In accordance with another aspect, the information obtained from at least one of the single scattering contribution and the multiple scattering contribution consists of the single scattering contribution, and the fourth processing logic performs a depression detection algorithm that processes the single scattering contribution to identify one or more lesions.

In accordance with another aspect, an ultrasound evaluation method for detecting lesions or abnormalities in a heterogeneous medium is provided. The method comprises:

with an array of ultrasound transducer elements, emitting ultrasound signals toward a region of biological tissue and receiving backscattered ultrasound signals;

with a processor configured to perform a lesion detection algorithm:

processing the received backscattered ultrasound signals to obtain Inter-element Response Matrix;

splitting the IRM into a plurality of sub-IRMs corresponding to subsets of the ultrasound transducer elements;

processing the sub-IRMs to separate a coherent intensity contribution from an incoherent intensity contribution; processing the coherent intensity contribution to obtain a diffusion constant; and performing a depression detection algorithm that processes the diffusion constant to identify one or more lesions.

In accordance with another aspect, the depression detection algorithm performed by the fifth processing logic identifies a plurality of potential lesions and detects a depression depth of each identified lesion, and the method further comprises performing a thresholding operation that that only treats the detected lesion having the greatest depression depth as a real lesion.

In accordance with another aspect, the method further comprises performing a Gaussian filter operation on the lesion that has the greatest depth to approximate a location and a size of the lesion that has the greatest depth.

In accordance with another aspect, an ultrasound evaluation method for detecting lesions or abnormalities in a heterogeneous medium is provided that comprises:

with an array of ultrasound transducer elements, emitting ultrasound signals toward a region of a biological tissue and receiving backscattered ultrasound signals;

with a processor configured to perform a lesion detection algorithm:

processing the received backscattered ultrasound signals to obtain an Inter-element Response Matrix;

splitting the IRM into a plurality of sub-IRMs corresponding to subsets of the ultrasound transducer elements;

processing the sub-IRMs to separate single scattering contributions from multiple scattering contributions; and processing information obtained from at least one of the single scattering contribution and the multiple scattering contribution to identify one or more lesions.

In accordance with another aspect, the information obtained from at least one of the single scattering contribution and the multiple scattering contribution comprises a ratio of the single scattering contribution to the multiple scattering contribution, and wherein the ratio is processed with a depression detection algorithm to identify one or more lesions.

In accordance with another aspect, the information obtained from at least one of the single scattering contribution and the multiple scattering contribution consists of the single scattering contribution, and the single scattering contribution is processed with a depression detection algorithm to identify one or more lesions.

In accordance with another aspect, a computer program for detecting lesions or abnormalities in a heterogeneous medium is provided. The computer program comprises computer instructions for execution by a processor that are embodied on a non-transitory computer-readable medium. The computer instructions comprise a first set of instructions for processing backscattered ultrasound signals received in the processor for an array of ultrasound transducer elements to obtain an IRM, a second set of instructions for splitting the IRM into a plurality of sub-IRMs corresponding to subsets of the ultrasound transducer elements, a third set of instructions for processing the sub-IRMs to separate a coherent intensity contribution from an incoherent intensity contribution, a fourth set of instructions for processing the coherent intensity contribution to obtain a diffusion constant, and a fifth set of instructions for performing a depression detection algorithm that processes the diffusion constant to identify one or more lesions.

In accordance with another aspect, the computer instructions comprise a first set of instructions for processing backscattered ultrasound signals received from an array of emitter and receiver transducer elements to obtain an IRM, a second set of instructions for splitting the IRM into a plurality of sub-IRMs corresponding to subsets of the ultrasound transducer elements, a third set of instructions for processing the sub-IRMs to separate single scattering contributions from multiple scattering contributions, and a fourth set of instructions for obtaining information from one or more of the single scattering contribution and the multiple scattering contribution processing the information to identify one or more lesions.

In accordance with another aspect, the information obtained from one or more of the single scattering contribution and the multiple scattering contribution comprises a ratio of the single scattering contribution to the multiple scattering contribution, and the fourth set of instructions performs a depression detection algorithm that processes the ratio of the single scattering contributions to multiple scattering contributions to identify one or more lesions.

In accordance with another aspect, the information obtained consists of the single scattering contribution, and the fourth set of instructions processes the single scattering contribution with a depression detection algorithm to identify one or more lesions A few representative embodiments of the NDE system and method will now be described with reference to FIGS. 1-10, in which like reference numerals represent like components, elements or features. It should be noted that features, elements or components in the figures are not intended to be drawn to scale, emphasis being placed instead on demonstrating inventive principles and concepts. It should be noted that the inventive principles and concepts are not limited to the representative embodiments described herein, as will be understood by those of skill in the art in view of the description provided herein.

In the following detailed description, for purposes of explanation and not limitation, exemplary, or representative, embodiments disclosing specific details are set forth in order to provide a thorough understanding of inventive principles and concepts. However, it will be apparent to one of ordinary skill in the art having the benefit of the present disclosure that other embodiments according to the present teachings that are not explicitly described or shown herein are within the scope of the appended claims. Moreover, descriptions of well-known apparatuses and methods may be omitted so as not to obscure the description of the exemplary embodiments. Such methods and apparatuses are clearly within the scope of the present teachings, as will be understood by those of skill in the art. It should also be understood that the word "example," as used herein, is intended to be non-exclusionary and non-limiting in nature.

The terminology used herein is for purposes of describing particular embodiments only, and is not intended to be limiting. The defined terms are in addition to the technical, scientific, or ordinary meanings of the defined terms as commonly understood and accepted in the relevant context.

The terms "a," "an" and "the" include both singular and plural referents, unless the context clearly dictates otherwise. Thus, for example, "a device" includes one device and plural devices. The terms "substantial" or "substantially" mean to within acceptable limits or degrees acceptable to those of skill in the art. The term "approximately" means to within an acceptable limit or amount to one of ordinary skill in the art.

The terms "memory," "memory device" or "memory system," as those terms are used herein, are intended to denote a non-transitory computer-readable storage medium that is capable of storing computer instructions, or computer code, for execution by one or more processors. References herein to "memory," "memory device" or "memory system," should be interpreted as one or more memories, memory devices or memory systems. The memory may, for example, be multiple memories within the same computer system. The memory may also be multiple memories distributed amongst multiple computer systems or computing devices.

A "processor," "processing device," or "processing logic," as those terms are used herein, are interchangeable and encompass at least one electronic device that is configured to perform one or more processing algorithms that process signals. The electronic device(s) may perform the algorithm(s) in hardware, software or firmware, or a combination thereof. References herein to a system comprising "a processor" or "a processing device" or "processing logic" should be interpreted as one or more processors or processing cores. The processor may, for instance, be a multi-core processor. A processor may also refer to a collection of processors within a single computer system or distributed amongst multiple computer systems. Instructions of a computer program can be performed by a single processor or by multiple processors that may be within the same device or that may be distributed across multiple devices. The term "controller," as that term is used herein, denotes an electronic device that comprises a processor, a processing device or processing logic, as those terms are defined herein.

FIG. 1 is a block diagram of the ultrasound system 1 in accordance with a representative embodiment. Because it is known how ultrasound systems acquire ultrasound signals, a detailed discussion of the acquisition process is not provided herein in the interest of brevity. A processor 10 of the ultrasound system 1 outputs control signals to an array of emitter and receiver ultrasound transducer elements 20 to control the ultrasound image acquisition process. The emitter ultrasound transducer elements of the array 20 emit ultrasound waves that propagate into the heterogeneous medium, which may be any type of biological tissue, living tissue or dead tissue, of any type of subject, human or non-human. The ultrasound waves are reflected, or back scattered, by scatterers within the medium. The back scattered ultrasound waves are received by the receiver transducer elements of the array 20 and converted into electrical ultrasound signals, which are then output to the processor 10 for processing. Additional electrical circuitry not shown in FIG. 1 for ease of illustration may be interposed in between the processor 10 and the array 20 for processing electrical signals output by the processor 10 to the array 20 (e.g., digital-to-analog conversion, amplification, etc.) and/or for processing the ultrasound electrical signals output from the array 20 to the processor (e.g., analog-to-digital conversion, amplification, etc.). The processor 10 performs a lesion detection and localization algorithm 30 that receives the ultrasound electrical signals and processes the signals to perform lesion detection and localization. Embodiments of the algorithm are discussed below in detail.

The ultrasound system 1 typically a memory device 40 for storing data and computer instructions for processing and execution by the processor 10. The lesion detection and localization algorithm 30 may be implemented in hardware, software or firmware, or a combination thereof. The system 1 may also include a display device 50 for displaying information to a user of the system 1 and a user interface (UI) 60.

First processing logic of the processor 10 processes the received backscattered ultrasound signals to obtain an Inter-element Response Matrix (IRM). Second processing logic of the processor 10 splits the IRM into a plurality of sub-IRMs corresponding to subsets of the ultrasound transducer elements. In accordance with a first representative embodiment, third processing logic of the processor 10 processes the sub-IRMs to separate a coherent intensity from an incoherent intensity. Fourth processing logic of the processor 10 processes the incoherent intensity to obtain a diffusion constant. Fifth processing logic of the processor 10 performs a depression detection algorithm that processes the diffusion constant to detect and localize one or more lesions.

In accordance with a second representative embodiment, after the third processing logic processes the sub-IRMs to separate the coherent intensity from the incoherent intensity, the fourth processing logic of the processor 10 processes the coherent intensity instead of the incoherent intensity to obtain the diffusion constant. The fifth processing logic then performs the depression detection algorithm that processes the diffusion constant to detect and localize one or more lesions.

It should be noted that although the system and method are being described herein as being used to detect lesions, they may be used to detect and localize any abnormalities in the complex media.

In accordance with a third representative embodiment, the third processing logic is configured to process the sub-IRMs to separate single scattering from multiple scattering contributions. The fourth processing logic is configured to obtain the ratio of single scattering to multiple scattering contributions. In accordance with this embodiment, the fifth processing logic is configured to perform a depression detection algorithm that processes the ratio of single scattering to multiple scattering contributions to identify one or more lesions and/or abnormalities.

In accordance with a fourth representative embodiment, the third processing logic is configured to process the sub-IRMs to separate single scattering from multiple scattering contributions. The fourth processing logic is configured to perform a depression detection algorithm that processes the single scattering contribution to identify one or more lesions and/or abnormalities.

One of the primary objectives of the inventive principles and concepts is to provide an algorithm capable of detecting and localizing weakly scattering regions in highly scattering media. For very strong scatterers, such as air pockets in water (similar to the lung parenchyma), traditional B-Scan ultrasound methods fail due to presence of multiple scattering and aberration effects. Also, TFM and DORT methodologies individually fail when multiple scattering dominates. In the presence of a highly porous medium and strong scatterers (steel, air, etc.), if the weakly scattering region is located a distance from the array significantly larger than the scattering mean free path, it is traditionally not possible to evaluate it with the currently available techniques.

The present disclosure describes a representative embodiment of a methodology that takes advantage of these multiple scattering signals in order to map the complex medium and detect the presence, size and shape of a target/lesion, or a weakly scattering region. For simulation purposes, water was used as a propagating medium in the presence of air scatterers as the heterogeneity with a varying porosity of 10%-50%. The target here was an anechoic lesion (simply a region of absence of air scatterers) whose size and depth were varied. The transducer array 10 was placed at a distance of 3 mm (near-field) from the surface of the random medium and the central frequency of the emitted pulse was 5 MHz. A 2 cycle pulse was sent from the element i and the backscattered signal was recorded by the element j, and this was repeated for every emitter receiver transducer element combination possible. This resulting matrix of backscattered signals is referred to herein as the Inter-element Response Matrix (IRM) H(t).

Once the IRM is obtained, it is split into sub-IRMs to obtain access over the spatial domain (i.e., the transducer axis). The backscattered intensity then provides access to the growth of the diffusive halo from the incoherent contribution. Once a two-dimensional (2-D) map of the variance is obtained, a known depression detection filter is applied to identify the regions of depression, thereby providing an estimate of the location and size of the target. For experiments, the inventors used a traditional 128 element linear array kept in the near field of a sponge/melamine foam media which has been modified to obtain desired porosity and has an anechoic lesion which has been made using petroleum jelly.

Basic Principle

Data Acquisition

In accordance with an embodiment, the array of ultrasound transducer elements is an N-element linear array. It should be noted that it is not necessary to use a linear array 20 or any particular array configuration. For example, the array 20 could be linear or curved and could be external or endocavitary. An endocavitary array could be disposed on the portion of an endoscope that is inserted into the medium being evaluated. The array 20 could be placed in a catheter and used endoscopically.

For the simulations and experiments presented here, 2 cycle pulses with a central frequency of 5 Megahertz (MHz) were transmitted from the emitter i and received by all the transducers j=1:N. This enabled the acquisition of the IRM represented by H(t) whose dimensions are N*N*t, the individual elements of which are $h_{ij}(t)$. The individual elements $h_{ij}(t)$ are the $N^2$ inter-element responses of the probe-medium system (transport parameters for an ultrasonic pulsed wave propagating in a heterogeneous medium). It should be noted that the inventive principles and concepts are not limited to the value of N, the value of the central frequency or the number of cycle pulses that are used.

Once the IRM is obtained, the IRM is split into sub-IRMs with a number, P, of elements (P=33 for simulations, P=43 for experiments). There will always be two or more sub-IRMs. The number of transducer elements P in each sub-IRM can be any number greater than one, but P will typically be a number greater than 33 or 43 used in the simulations and experiments, respectively. For purposes of explanation, it is assumed that P=33 and N=96. When the IRM is split into sub-IRMs, each sub-IRM is referred to herein as $H_z(t)$, where z ranges from $$\frac{P+1}{2} \text{ to } \frac{2N-P+1}{2}.$$

Figure 2:
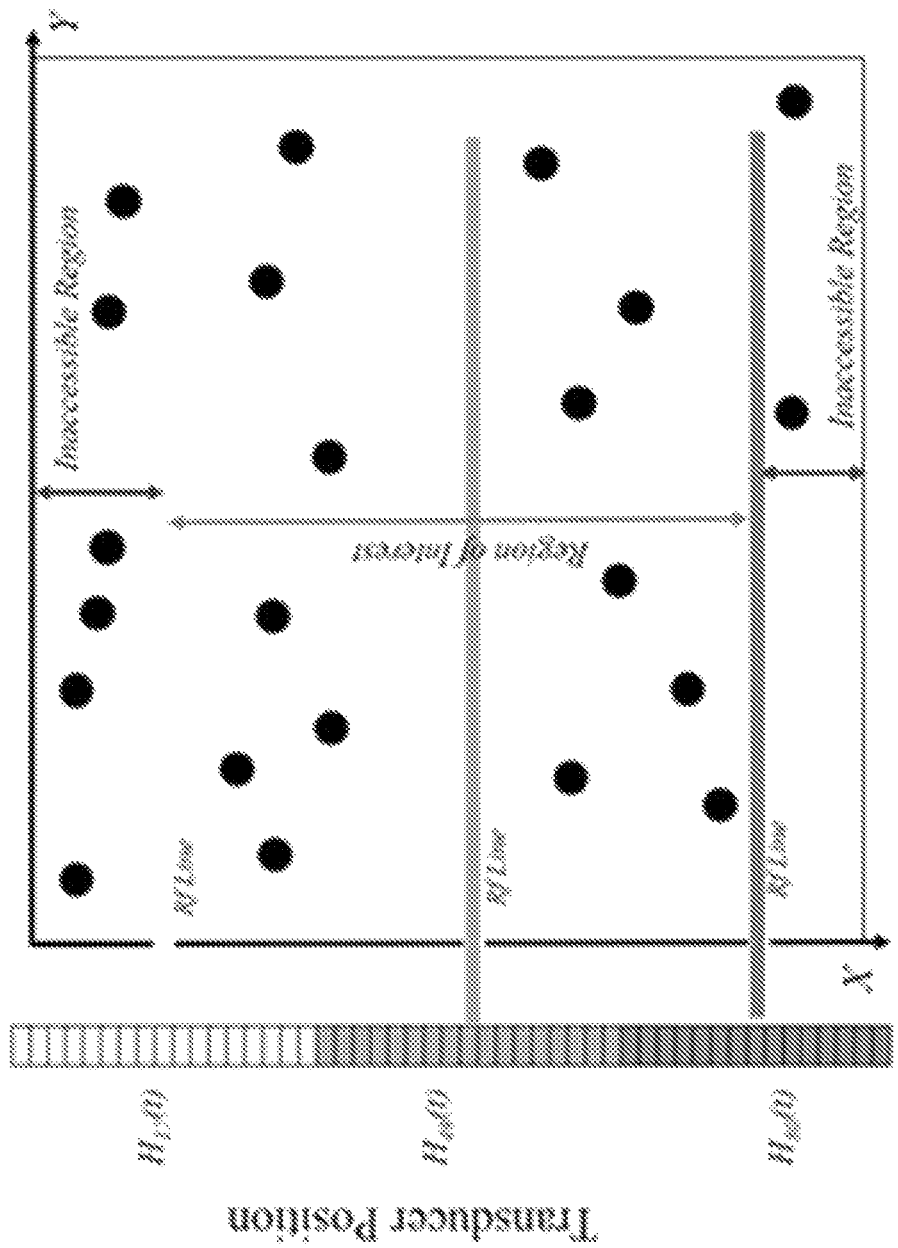
FIG. 2 is a representation of an ultrasound transducer array facing a heterogeneous medium; sub-arrays are represented on the array by different levels of gray, showing how sub Inter-element Response Matrices (sub-IRMs) can be acquired.

Hence the first the sub-IRM will be referred to as $H_{17}(t)$ and each element of this sub-IRM is $h^{17}_{ij}(t)$ where i ranges from 1:33 and j from 1:33. Hence, the dimension of $H_{17}(t)$ are 33*33*t. The superscript in $h^{17}_{ij}(t)$ has been set to 17 since that is the central element of the sub-IRM, and that is where counting would begin. If P=43, the counting would start from 22. Also, the index in the superscript informs of the location at which this matrix will give access to the variance plot. Hence, $H_{17}(t)$, when further processed, provides the growth of the diffusive halo at the transducer element location 17 and the depth will be accessed by the time signal. This can be imagined as having a small transducer with 33 elements which is then moved across the geometry to get a full spatial access of the random medium in consideration. This is shown in FIG. 2, which is a plot of transducer element position on the vertical X-axis and distance from the array 20 along the horizontal Y-axis for a plurality of sub-IRMs. In FIG. 2, $H_{17}(t)$, $H_{49}(t)$ and $H_{80}(t)$ will give the growth of the incoherent intensity for transducer element locations 17, 49 and 80. It is interesting to note here that the region in front of elements 1-16 and from 81-96 will have no representation by any sub-IRMs and are hence deemed to be inaccessible regions for image generation and backscattered intensity calculation.

Obtaining the Variance Plot and 2D Map

Figure 3:
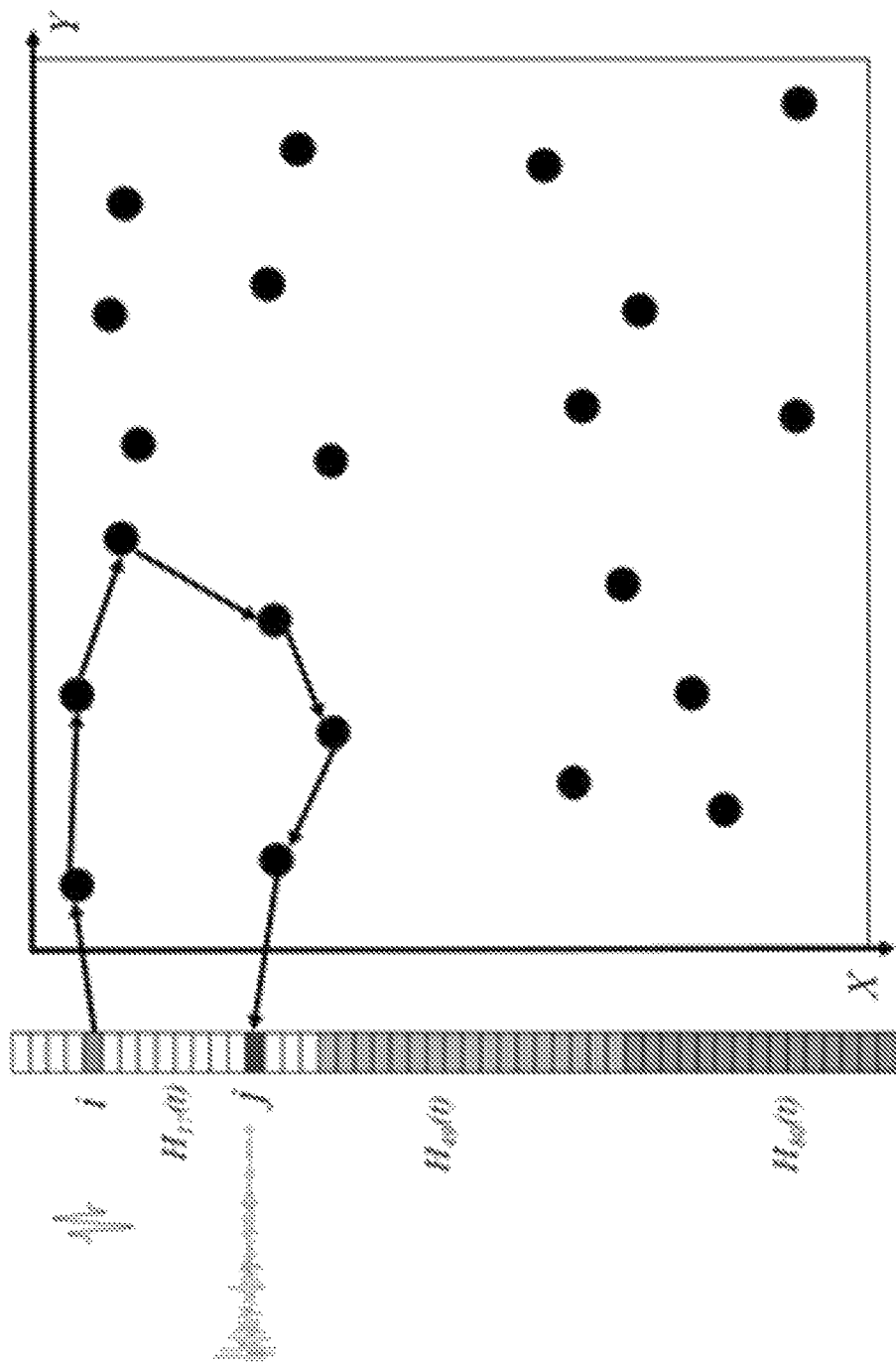
FIG. 3 is a representation of one of the many propagation paths in a complex heterogeneous medium, when a pulse is transmitted by element i, and the backscattered signals are recorded on element j.

Once all the sub-IRMs have been obtained, the backscattered intensity is calculated and split into its two constituents, the coherent and the incoherent intensities. In accordance with the first representative embodiment mentioned above, the incoherent backscattered intensity provides access to the diffusion constant. Every sub-IRM $H_z(t)$ has a specific reciprocity feature: $h^z_{ij}(t)=h^z_{ji}(t)$. Based on this property an anti-sub-IRM $H_z^A(t)$ is defined: for i>j, $h_{ij}^{zA}=-h_{ij}^z$; for i=j, $h_{ij}^{zA}=0$ and for i<j, $h_{ij}^{zA}=h_{ij}^z$. The backscattered intensity for $H_z(t)$ can be calculated by appropriately time shifting the signal and truncating it over 0.3 μs overlapping windows.

$$k_{ij}^z(T,t)=h_{ij}^z(T+t)*W_R(t),$$

where $W_R(t)=1$ for t=[0, 0.3 μs] and $W_R(t)=0$ everywhere else. Once $k^z ij(T,t)$ obtained, a short time FFT is executed to obtain the $K^z(T,f)$ for each time window T and the range of frequencies present in the bandwidth. Every element of $K^z(T,f)$ can be represented as $k^z_{ij}(T,f)$ which is the frequency response at f between emitter i and receiver j as shown in FIG. 3.

Note here that this $h^z_{ij}(T,f)$, which is in the frequency domain, is different from $k^z_{ij}(T,t)$, which is in the time domain. The backscattered intensity is then calculated by squaring $k^z_{ij}(T,f)$ and integrating them over emitter/receiver couples separated by the same distance X=|i−j|. The results are then summed over all frequencies to obtain the following equation:

$$F(X,T)=<|k_{ij}^z(T,f)|^2>_{f,\{ij\}}$$

The procedure to calculate the backscattered intensity can also be done in the time domain by squaring and integrating $k^z ij(T, t)$ over time and over emitter/receiver couples separated by the same distance X.

$$F(X,T)=<|k_{ij}^z(T,t)|^2>_{t,\{ij\}},$$

where $$i,j=\left(z-\frac{P-1}{2}, z+\frac{P-1}{2}\right)$$

for a fixed value of z.

The same mathematical procedure can be applied to obtain $I^{zA}(X,T)$ which is the backscattered intensity for the anti-sub-IRM. Note that $I^{zA}(X,T)$ doesn't have physical relevance and is purely made up for separating the coherent and incoherent intensities. The incoherent intensity is obtained by taking an average of $I^{zA}(X,T)$ and $I^z(X,T)$. Also, analytically it can be expressed as $$I_{inc}^z(X,T)=I^z(X,T)\exp\left(-\frac{X^2}{4D_zT}\right).$$

where X represents the distance between emitter and receiver and $D_z$ represents the local diffusion constant. It can be seen from the equation above that the exponential appears to be a Gaussian distribution. The obtained $I^2_{inc}(X,T)$ is a 2-D intensity matrix and is a function of T and $X=|i-j|$. At each time window, the incoherent intensity profile is fitted with a Gaussian curve and its variance ($W_z^2(T)=2D_zT$) is plotted with time. Half of the slope of the linear fit provides the diffusion constant for the location or domain located in front of the transducer element position Z. This can be repeated for all transducer element positions z ranging from $$\frac{P+1}{2} \text{ to } \frac{2N-P+1}{2}$$

to obtain the 2-D variance map, which is denoted by $W^2(z,T)$. A change of variable by associating T with the depth of propagation using the speed of sound $C_0$ leads to the final 2-D variance map denoted by $W^2(z,y)$, where z represents the transducer axis and y represents the depth of the wave propagation.

Firstly a 1-D map of the diffusion constant along the transducer axis can be obtained by fixing z and taking a linear slope of the variance $W_z^2(T)$ to obtain the local diffusion constant, $D_z$. $D_z$ provides the diffusivity of the media in that specific Rf line. The diffusion constant is an accurate representation of the extent of heterogeneity and scatterer volume fraction of the medium. Secondly, the changes of the diffusion constant along the transducer, or the 1-D map, provides a fair estimate of the extent of anisotropy in the medium. This feature of the 1-D map is discussed below in more detail. Multiple 1-D maps obtained by rotating the angle of the transducer array with respect to the surface of the medium can be compounded and combined to create a 2-D map of the Diffusion Constant, which would enable detection and localization a lesion or abnormality. This latter approach, and variations of it, can be used with any of the four embodiments described herein.

Target Detection Using Image Processing

The growth of the variance with time ($W_z^2(T)$) when fitted with a linear slope provides the diffusion constant $D_z$. However, what is interesting to note here is that, as the wave propagates straight and goes deeper in the random medium, the diffusive regime becomes stronger. The linear trend of the variance over time is well captured, which showcases the growth of the diffusive halo over time. However, when the propagating wave encounters an anechoic lesion or a region with no scatterers, it deviates from its linearly increasing trend. As the wave enters the region without scatterers, the diffusion constant increases and so does the slope of the variance curves. The gradual or sudden increase in the variance is what enables the location of the anechoic lesion to be tracked. These deviations are treated as outliers that need to be isolated. To accomplish this, two new matrices or 2-D fields are defined as follows:
1. Linear Fit Field (L (z,y)): Map generated from doing a line by line, linear regression fit of $W^2(z,y)$. The linear fit can also be replaced by any 1-D smoothing algorithm. The purpose of the smoothing or linear fit is to have a perfect linearly-growing diffusive halo trend such that it can be differentiated from a variance plot, which has values deviating from the linear trend.
2. Delta Field ($\Delta(z,y)$): Map showcasing the outliers in the variance map.

$$\Delta(z,y)=1-\max(W^2(z,y)-L(z,y))$$

The delta field is a representation of the outlier map. In an ideal case, the outliers will form a closed enclosure which needs to be extracted in order to map the anechoic lesion. On the delta map, a known depression detection filter (DDF) algorithm is applied. The DDF algorithm was initially developed to determine where pools of water would form on a surface if the drainage point were the edge of the surface. The DDF algorithm treats the outside edges of the closed loop enclosure/depression as the edges which act as the drainage. Theoretically it is a water-filling algorithm. All the local low-points are determined and the water starts filling until the water flows off the surface and reaches the edge. All the points outside the edge are treated as a negative infinity and the depression is then determined. The DDF algorithm uses the nearest eight neighboring points to detect the enclosure/depression, but for faster speed, the four neighboring points may be used instead, although it will result in a compromise in accuracy.

Threshold and Size Prediction

Once the location and approximate size of the lesion has been identified, a major challenge confronted is the under-prediction of the size of the lesion and isolating the actual lesion from the surrounding noise. The DDF algorithm may predict the existence of other lesions, which are in reality just noise. This issue is resolved by applying a threshold on the normalized delta map after the application of the DDF algorithm. The threshold only keeps the lesion with the maximum depth and eliminates all other lesions. The major disadvantage of the thresholding is the fact that if there are two lesions of different sizes lying near each other, the threshold might ignore the existence of one of the anechoic lesions considering it to be noise. As a remedy, an iterative approach could be implemented, using different, subsequent thresholds.

Once the lesion has been isolated, a normal Gaussian filter is applied in order to obtain an estimate on the actual size of the nodule. Based on the variation of the diffusion constant $D_z$ along the transducer, a rough estimate of the size of the lesion can be obtained. Based on this initial guess, the Gaussian filter of the desired order is applied to smoothen the edges of the identified lesion. In these simulations, lesion sizes of 5 mm, 8 mm and 10 mm were simulated, based on the initial guess of the 1-D diffusion constant map, a second-order filter was applied for nodule sizes of 5 mm and 8 mm and a third-order filter was applied for a nodule size of 10 mm.

Figure 4:
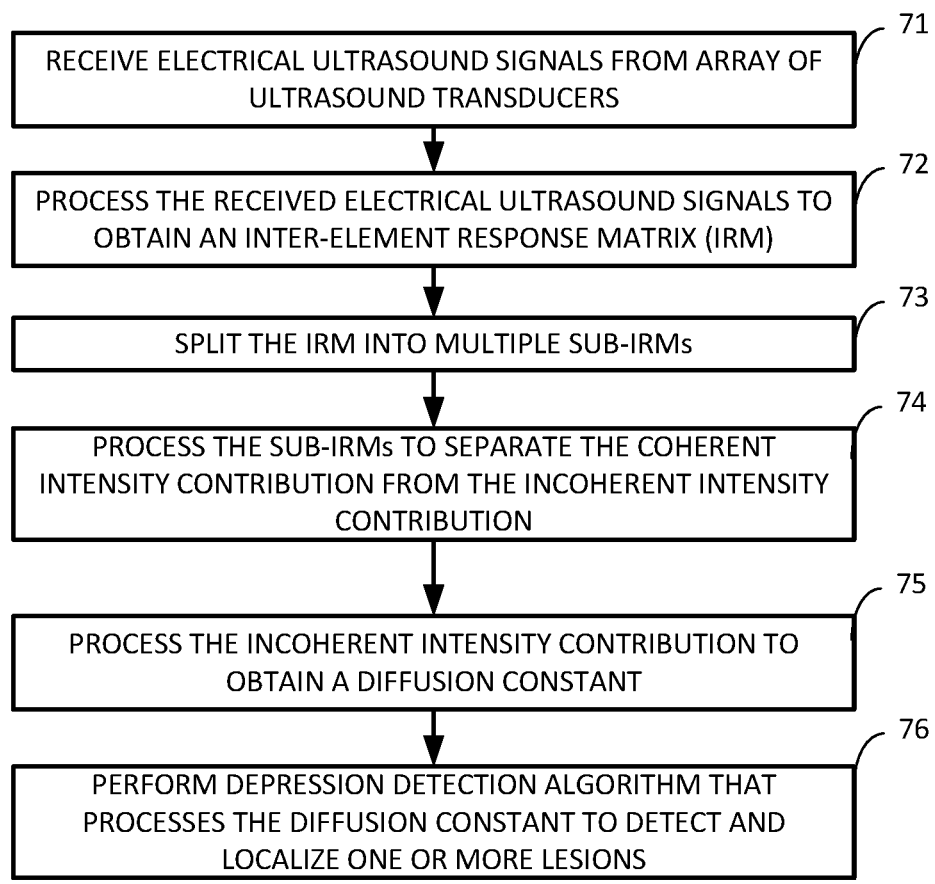
FIG. 4 is a flow diagram representing the lesion detection and localization algorithm performed by the processor shown in FIG. 1 in accordance with a first representative embodiment.

FIG. 4 is a flow diagram representing the lesion detection and localization algorithm performed by the processor 10 in accordance with the aforementioned first representative embodiment. The processor 10 receives the backscattered ultrasound signals from the array of emitter and receiver transducer elements 20, as indicated by block 71. The received backscattered ultrasound signals are processed to obtain an IRM, as indicated by block 72. The IRM is split into a plurality of sub-IRMs corresponding to subsets of the ultrasound transducer elements, as indicated by block 73. The sub-IRMs are processed to separate the coherent intensity contribution from the incoherent intensity contribution, as indicated by block 74. The incoherent intensity contribution is processed to obtain a diffusion constant, as indicated by block 75. A depression detection algorithm is then performed that processes the diffusion constant to detect and localize one or more lesions, as indicated by block 76.

Figure 5:
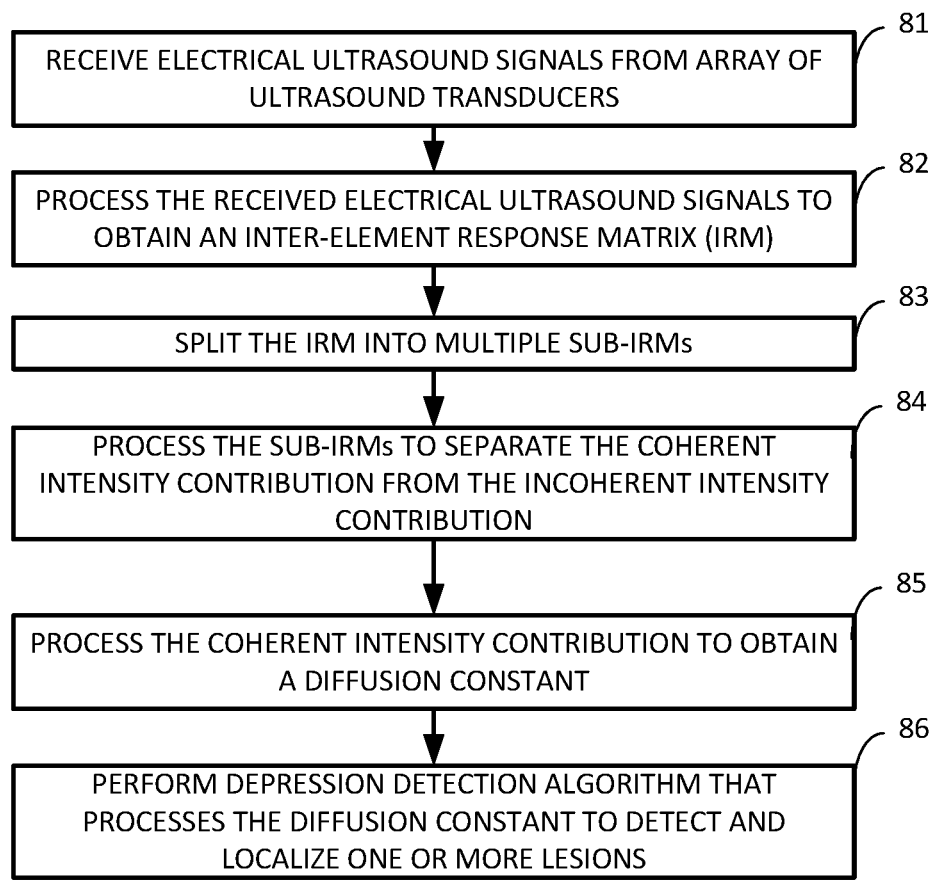
FIG. 5 is a flow diagram representing the lesion detection and localization algorithm performed by the processor shown in FIG. 1 in accordance with a second representative embodiment.

FIG. 5 is a flow diagram representing the lesion detection and localization algorithm performed by the processor 10 in accordance with the second representative embodiment. Blocks 71-74 and 76 shown in FIG. 4 are identical to blocks 81-84 and 86, respectively, shown in FIG. 5. Blocks 75 and 85 are only different in that block 85 corresponds to processing the coherent intensity contribution instead of the incoherent intensity contribution to obtain the diffusion constant. The algorithm used in block 85 will now be described in detail.

Figure 6:
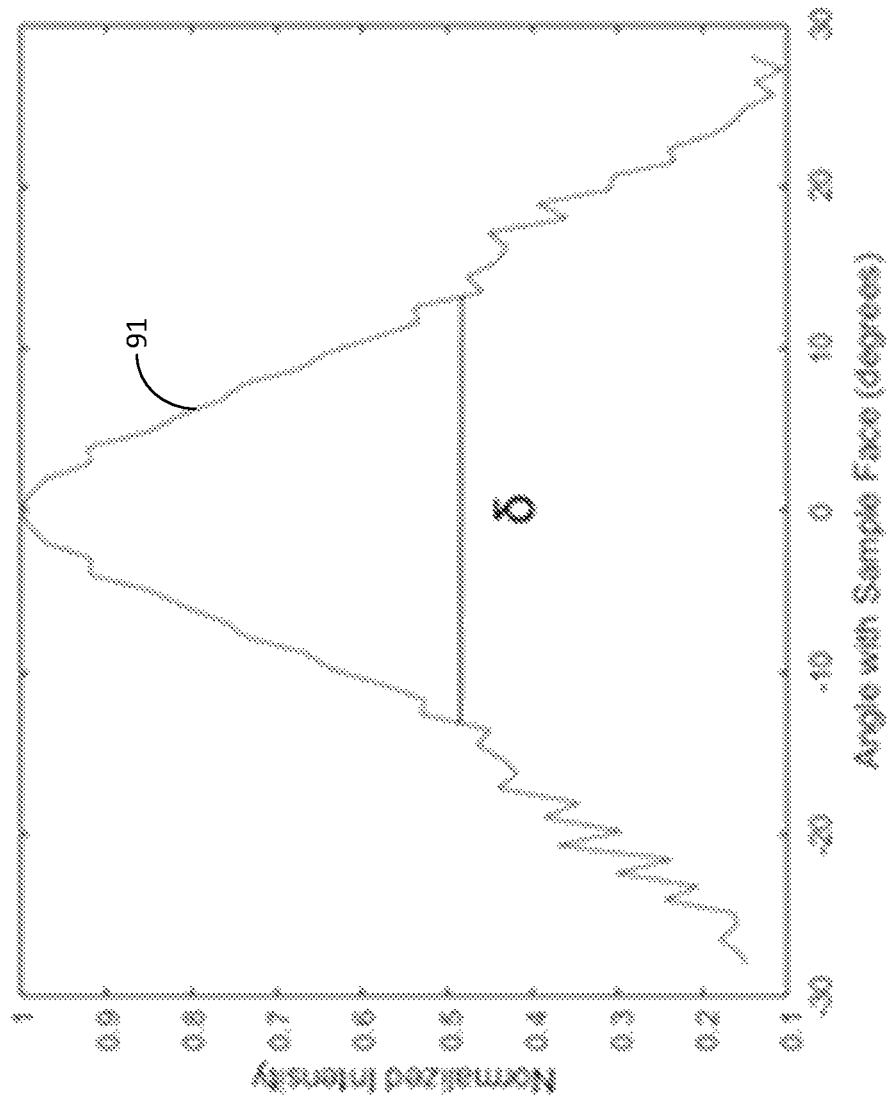
FIG. 6 is graph that shows an example of a coherent intensity peak fitted with a Gaussian curve.
Figure 7:
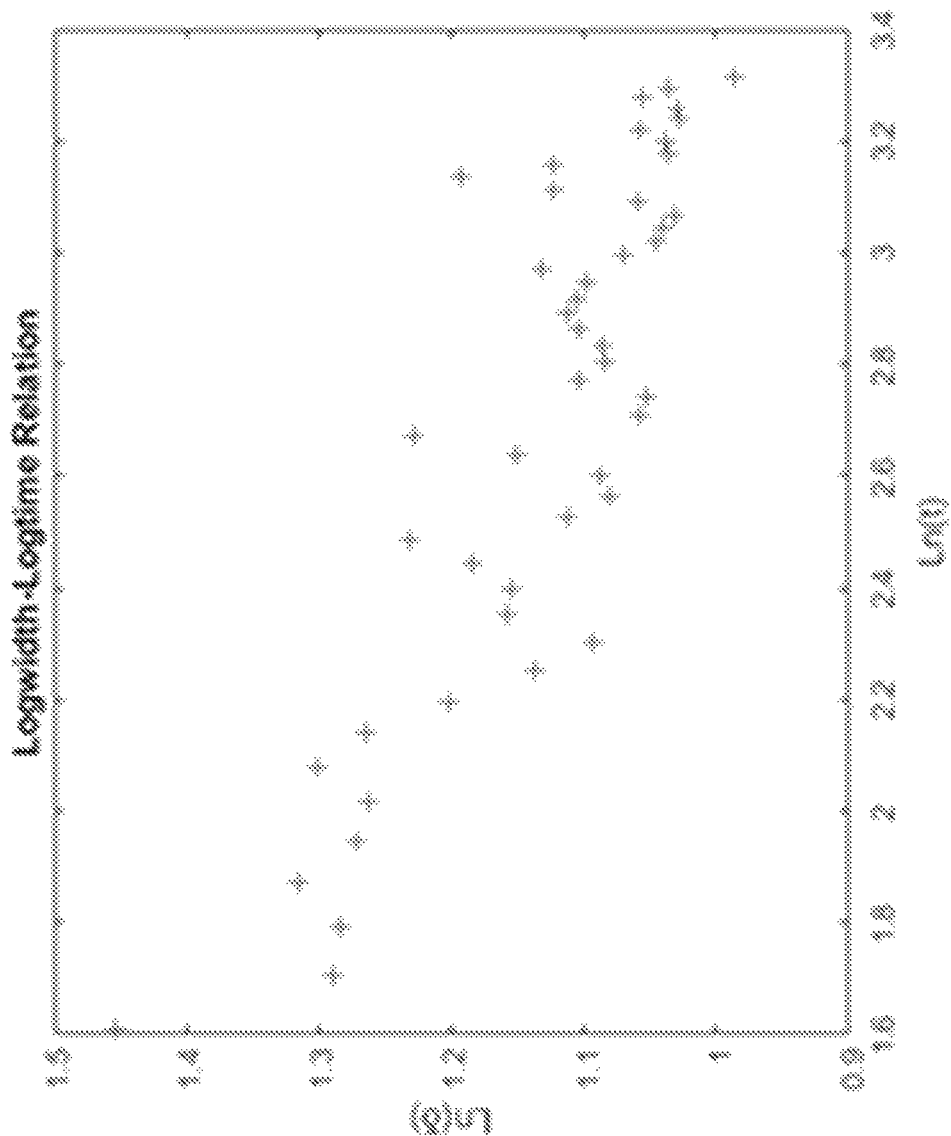
FIG. 7 is a graph showing the natural logarithm of the widths of coherent intensity peaks such as that shown in FIG. 6 plotted against the natural logarithm of each time window.

The coherent intensity contribution cannot be used in the near field, and therefore the array 20 will have to be move slightly farther away from the heterogeneous medium being inspected. The principle of the algorithm is as follows. For each time window of the coherent intensity matrix, the coherent peak can be fitted with a Gaussian curve. FIG. 6 is graph that shows an example of a coherent peak 91 fitted with a Gaussian curve. Once the standard deviation for each Gaussian fit is stored, these standard deviations can be used to calculate the full width at half maximum via the following equation: $\delta=\sqrt{2\ln 2}\sigma=2.355\sigma$, where $\delta$ is the full width shown in FIG. 6 at half maximum and $\sigma$ is the standard deviation. FIG. 7 is a graph showing the natural logarithm of the widths plotted against the natural logarithm of each time window. While the coherent peak 91 contains an ensemble average of only three measurements, there is still a fairly noticeable negative correlation in the data as could be predicted: the coherent peak 91 narrows over time. A linear fit of the points shown in FIG. 7 provides an estimate of the log-width intercept. From this intercept, the diffusion constant may be found through the following equation: In $$\delta = 1.12 \frac{1}{k\sqrt{D\ln t}},$$

where k is the wavenumber of the emitted wave. Along with each linear fit, the 95% confidence interval of each intercept calculation was stored in order to provide a level of uncertainty in each measurement.

Figure 8:
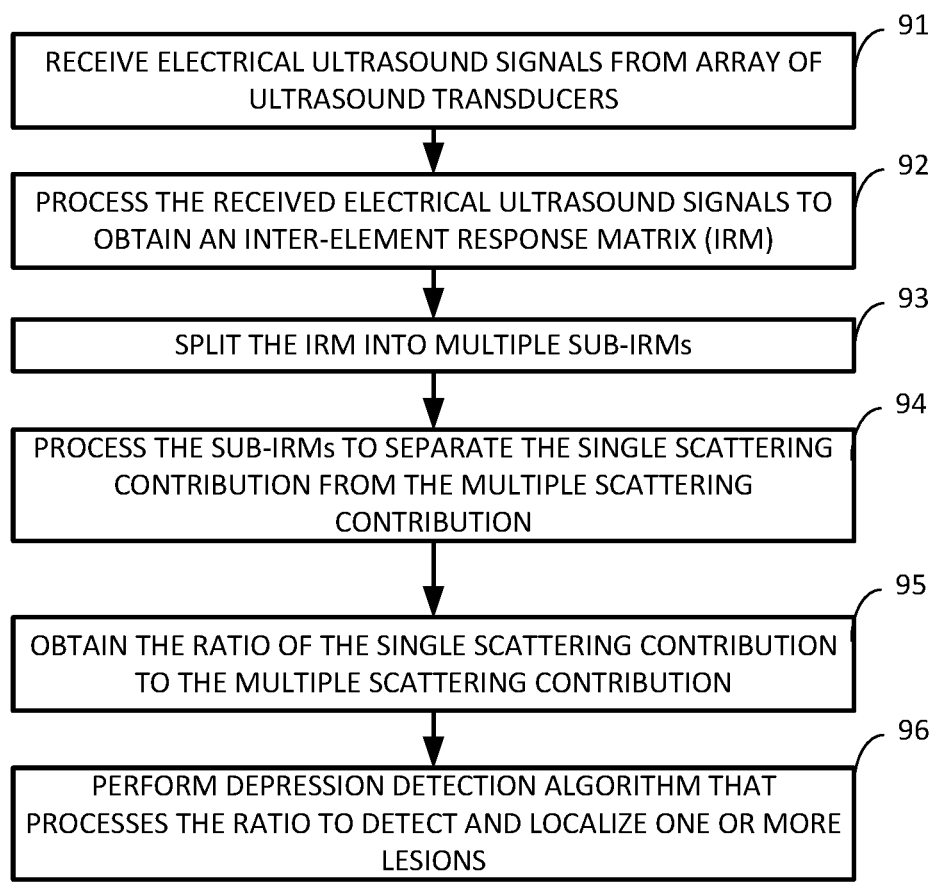
FIG. 8 is flow diagram representing the lesion detection and localization algorithm performed by the processor shown in FIG. 1 in accordance with a third representative embodiment.

FIG. 8 is flow diagram representing the lesion detection and localization algorithm performed by the processor 10 in accordance with the aforementioned third representative embodiment. Blocks 71-73 shown in FIG. 4 are identical to blocks 91-93, respectively, shown in FIG. 8. In accordance with this representative embodiment, processor 10 processes the sub-IRMs at block 94 to separate single scattering contributions from multiple scattering contributions. At block 95, the processor 10 obtains the ratio of single scattering contributions to multiple scattering contributions. At block 96, the processor 10 performs the depression detection algorithm that processes the ratio of single scattering to multiple scattering contributions to identify one or more lesions and/or abnormalities. The algorithm of block 94 will now be described in detail.

Step 1: Truncation into Time Windows and Conversion into Fourier Domain

After the IRM is obtained, the time signals hij(t) are truncated in overlapping time windows. In this example, 1.2 µs overlapping time windows are used. The following equation represents the truncation: kij(T,t)=hif(T+t)*WR(t) with WR(t)=1 for t≡[0,1.2 µs] and WR(t)=0 elsewhere. A short time Fast Fourier Transform (FFT) is then performed on the truncated data to obtain a response matrix called (T,) for each time window T. Each element of (T,) is represented as (T,f) corresponding to the responses at the frequency f and time T between the emitter location (i=XE) and the receiver location (j=XR). As an example, the K matrix at a given time window T and frequency exhibits coherence along its anti-diagonals. K(T,t) is then converted to K(T,f) whose elements are given by kij(T,f), where kij(T,f)=kifS(T,f)+kifM(T,f).

Step 2: Matrix Rotation

Two matrices A1 and A2 are built:

A1=[a1uv] of dimension (2M−1)×(2M−1), such that a1[u, v]=k[u+v−1, v−u+2M−1].

A2=[a2uv] of dimension (2M−2)×(2M−2), such that a2[u, v]=k[u+v, v−u+2M−1], where M=(N+3)/4. Here N=125 and so M=32 is an even number. A1 and A2 correspond to the antidiagonals of (T,f). For A1, the dimensions are LA1=2M−1 and for A2, the dimensions are LA2=2M−2. A is now invariably used for both A1 and A2 and L for both LA1 and LA2.

Step 3: Singular Value Decomposition (SVD)

SVD is applied to the matrix A (A1 or A2).

$$A = U \wedge V^+ = \Sigma_{k=1}^{M} \lambda_k U_k V_k^+$$

Step 4: Cutoff Eigen Value for Determination of SS and MS Contributions

Figure 9:
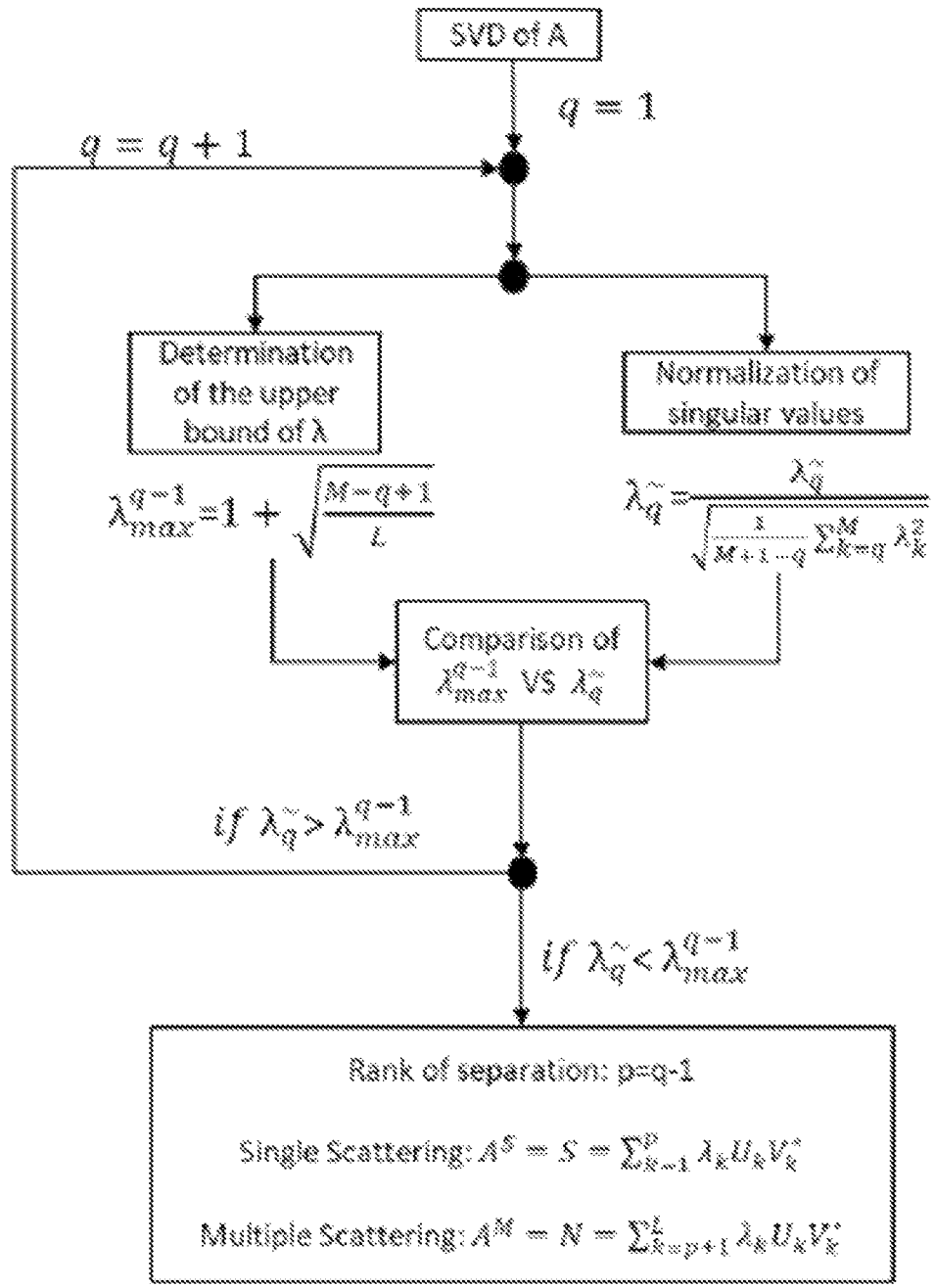
FIG. 9 is a flow diagram representing portions of the algorithm represented by blocks 94-96 of the flow diagram of FIG. 8.

Once the eigen values $\lambda_k$ have been identified in step 4, the cutoff which will separate the multiple and single scattering contributions is determined in an iterative process according to the flow chart shown in FIG. 9. Because it is believed that the flow chart is self-explanatory in that it identifies the mathematic operations corresponding to each block, it is not described in further detail herein.

Step 5:

This step is the reverse of Step 2. From AS and AM, two matrices, KS and KM, are built with a change of coordinates.

if (i−j)/2 is an integer, then, kS,M[i, j]=a1S,M [(i−j)/2+M,(i+j)/2]

if (i−j)/2 is not an integer, then, kS,M[i, j]=a2S,M [(i−j−1)/2+M,(i+j−1)/2]

KS contains the single scattering contribution (plus a residual multiple scattering contribution) and KM contains the multiple scattering contribution.

Step 6: Obtaining Backscattered Intensity IS, IM and ITotal

The backscattered intensities can be obtained using the following equation:

$$I^{S,M,Tot} = <|k_{i,j}^{S,M,Tot}(T,f)|^2>_{f,[(i,j)|m=j-i]}$$

The above equation denotes that the amplitudes in the K matrix and squared, summed over all frequencies and averaged over all emitter/receiver transducer element couples separated by the same distance. Having performed Steps 1-6 to separate the single scattering and the multiple scattering contributions from one another, the processes represented by blocks 95 and 96 are performed to complete the process.

Figure 10:
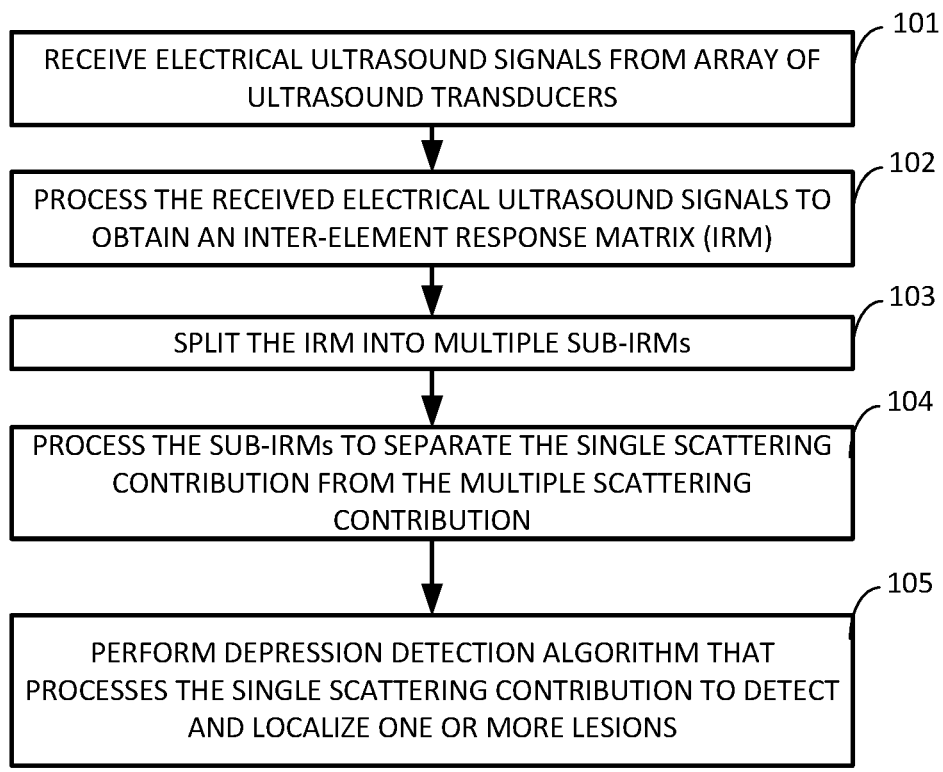
FIG. 10 is flow diagram representing the lesion detection and localization algorithm performed by the processor shown in FIG. 1 in accordance with a fourth representative embodiment.

FIG. 10 is a flow diagram representing the lesion detection and localization algorithm performed by the processor 10 in accordance with the aforementioned fourth representative embodiment. Blocks 91-94 shown in FIG. 8 are identical to blocks 101-104, respectively, shown in FIG. 8. In accordance with this representative embodiment, at block 105, the processor 10 performs the depression detection algorithm that processes the single scattering contribution to identify one or more lesions and/or abnormalities.

Figures 11A, 11B:
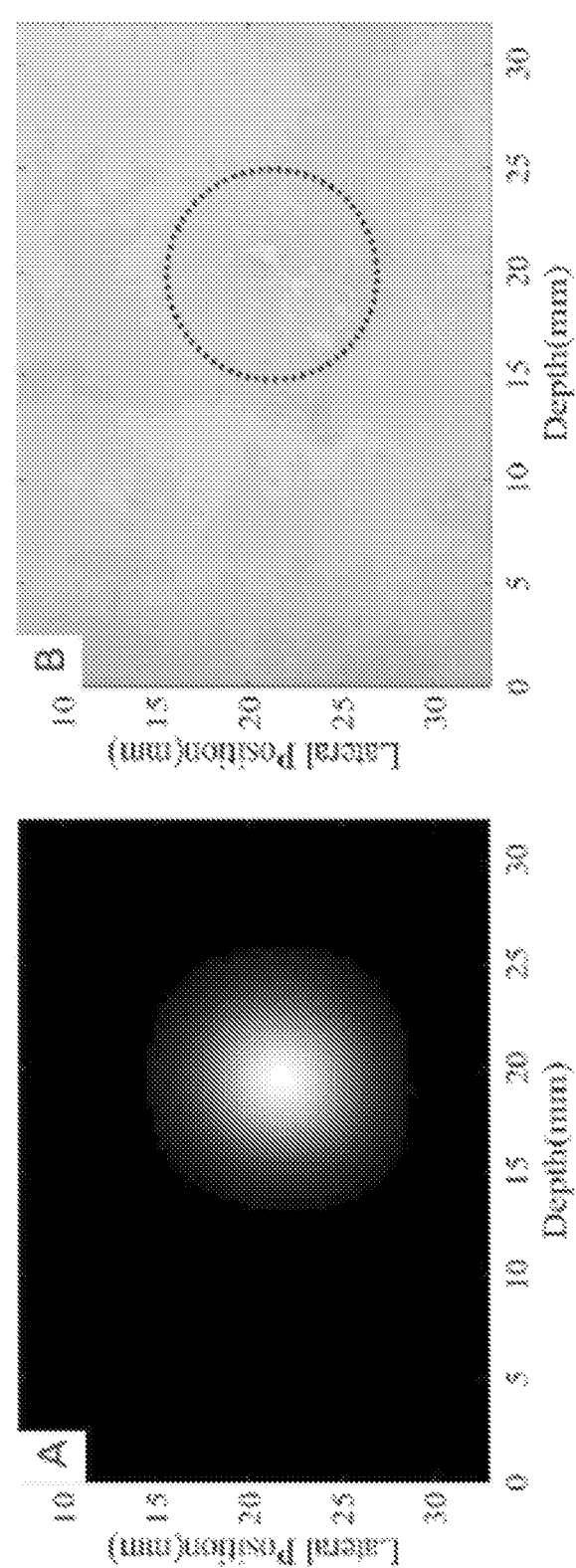
FIG. 11A shows an image rendered by the ultrasound system shown in FIG. 1 demonstrating the detection of a "lesion" that was created by inserting a Vaseline nodule into a sponge.
FIG. 11B is a photograph of a sponge having a Vaseline lesion inside of it.

FIG. 11B is a photograph of a sponge having a Vaseline lesion inside of it. FIG. 11A shows an image rendered by the ultrasound system 1 shown in FIG. 1 demonstrating the detection and localization of the Vaseline lesion shown in FIG. 11B. It can be seen in FIG. 11A that the system 1 and methods described above all the lateral position and depth of the lesion in a complex scattering medium to be determined.

It should be noted that the inventive principles and concepts have been described with reference to representative embodiments, but that the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. An ultrasound system for detecting lesions or abnormalities in a heterogeneous medium, the system comprising:
   an array of ultrasound transducer elements configured to emit ultrasound signals and to receive backscattered ultrasound signals;
   a processor configured to perform a lesion detection algorithm, the processor comprising:
      first processing logic configured to process the received backscattered ultrasound signals to obtain an Inter-element Response Matrix (IRM);
      second processing logic configured to split the IRM into a plurality of sub-IRMs corresponding to subsets of the array of ultrasound transducer elements;
      third processing logic configured to process the plurality of sub-IRMs to separate a coherent intensity contribution from an incoherent intensity contribution;
      fourth processing logic configured to process the coherent intensity contribution to obtain a diffusion constant; and
      fifth processing logic configured to perform a depression detection algorithm that processes the diffusion constant to identify one or more lesions.

2. The system of claim 1, wherein the array of ultrasound transducer elements is a one-dimensional (1-D) array.

3. The system of claim 1, wherein the array of ultrasound transducer elements is a two-dimensional (2-D) array.

4. The system of claim 1, wherein the array of ultrasound transducer elements is a linear array.

5. The system of claim 1, wherein the array of ultrasound transducer elements is a curved array.

6. The system of claim 1, wherein the depression detection algorithm performed by the fifth processing logic identifies a plurality of potential lesions and detects a depression depth of each identified lesion, and wherein the processor further comprises:
   sixth processing logic configured to perform a thresholding operation that only treats the identified lesion having a greatest depression depth as a real lesion.

7. The system of claim 6, wherein the processor further comprises:
   seventh processing logic configured to perform a Gaussian filter operation on the identified lesion that has the greatest depth to approximate a location and a size of the identified lesion that has the greatest depth.

8. An ultrasound system for detecting lesions or abnormalities in a heterogeneous medium, the system comprising:
   an array of ultrasound transducer elements configured to emit ultrasound signals and to receive backscattered ultrasound signals;
   a processor configured to perform a lesion detection algorithm, the processor comprising:
      first processing logic configured to process the received backscattered ultrasound signals to obtain an Inter-element Response Matrix (IRM);
      second processing logic configured to split the IRM into a plurality of sub-IRMs corresponding to subsets of the array of ultrasound transducer elements;
      third processing logic configured to process the plurality of sub-IRMs to separate single scattering contributions from multiple scattering contributions; and
      fourth processing logic configured to process information obtained from at least one of the single scattering contribution and the multiple scattering contribution to identify one or more lesions.

9. The ultrasound system of claim 8, wherein said information obtained from at least one of the single scattering contribution and the multiple scattering contribution consists of a ratio of the single scattering contribution to the multiple scattering contribution, and wherein the fourth processing logic performs a depression detection algorithm that processes the ratio to identify the one or more lesions.

10. The ultrasound system of claim 8, wherein said information obtained from at least one of the single scattering contribution and the multiple scattering contribution consists of the single scattering contribution, and wherein the fourth processing logic performs a depression detection algorithm that processes the single scattering contribution to identify the one or more lesions.

11. The system of claim 8, wherein the array of ultrasound transducer elements is a one-dimensional (1-D) array.

12. The system of claim 8, wherein the array of ultrasound transducer elements is a two-dimensional (2-D) array.

13. The system of claim 8, wherein the array of ultrasound transducer elements is a linear array.

14. The system of claim 8, wherein the array of ultrasound transducer elements is a curved array.

15. An ultrasound evaluation method for detecting lesions or abnormalities in a heterogeneous medium, the method comprising:
   with an array of ultrasound transducer elements, emitting ultrasound signals toward a region of biological tissue and receiving backscattered ultrasound signals;
   with a processor configured to perform a lesion detection algorithm:
      processing the received backscattered ultrasound signals to obtain an Inter-element Response Matrix (IRM);
      splitting the IRM into a plurality of sub-IRMs corresponding to subsets of the ultrasound transducer elements;
      processing the plurality of sub-IRMs to separate a coherent intensity contribution from an incoherent intensity contribution;
      processing the coherent intensity contribution to obtain a diffusion constant; and
      performing a depression detection algorithm that processes the diffusion constant to identify one or more lesions.

16. The method of claim 15, wherein the depression detection algorithm identifies a plurality of potential lesions and detects a depression depth of each identified lesion, and wherein the method further comprises:
   performing a thresholding operation that that only treats the identified lesion having a greatest depression depth as a real lesion.

17. The method of claim 16, further comprising:
performing a Gaussian filter operation on the identified lesion that has the greatest depth to approximate a location and a size of the identified lesion that has the greatest depth.

18. An ultrasound evaluation method for detecting lesions or abnormalities in a heterogeneous medium, the method comprising:
with an array of ultrasound transducer elements, emitting ultrasound signals toward a region of a biological tissue and receiving backscattered ultrasound signals;
with a processor configured to perform a lesion detection algorithm:
processing the received backscattered ultrasound signals to obtain an Inter-element Response Matrix (IRM);
splitting the IRM into a plurality of sub-IRMs corresponding to subsets of the array of ultrasound transducer elements;
processing the plurality of sub-IRMs to separate single scattering contributions from multiple scattering contributions; and
processing information obtained from at least one of the single scattering contribution and the multiple scattering contribution to identify one or more lesions.

19. The ultrasound method of claim 18, wherein said information obtained from at least one of the single scattering contribution and the multiple scattering contribution comprises a ratio of the single scattering contribution to the multiple scattering contribution, and wherein the ratio is processed with a depression detection algorithm to identify the one or more lesions.

20. The ultrasound method of claim 18, wherein said information obtained from at least one of the single scattering contribution and the multiple scattering contribution consists of the single scattering contribution, and wherein the single scattering contribution is processed with a depression detection algorithm to identify the one or more lesions.

* * * * *